(12) United States Patent
Wang et al.

(10) Patent No.: US 7,869,034 B2
(45) Date of Patent: Jan. 11, 2011

(54) MULTI-ANGLE AND MULTI-CHANNEL INSPECTING DEVICE

(75) Inventors: Hau-Wei Wang, Taipei County (TW); Fu-Shiang Yang, Hsinchu County (TW); Yu-Shan Chang, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 805 days.

(21) Appl. No.: 11/734,794

(22) Filed: Apr. 13, 2007

(65) Prior Publication Data

US 2008/0043232 A1   Feb. 21, 2008

(30) Foreign Application Priority Data

Aug. 15, 2006   (TW) ............................. 95129853 A

(51) Int. Cl.
   *G01J 3/28* (2006.01)
(52) U.S. Cl. ...................................... 356/326
(58) Field of Classification Search ................. 356/326, 356/328
   See application file for complete search history.

(56) References Cited

U.S. PATENT DOCUMENTS

| 5,751,420 | A | 5/1998 | Iida et al. |
| 6,804,001 | B1 | 10/2004 | Leroux |
| 2003/0227628 | A1* | 12/2003 | Kreimer et al. ............ 356/419 |
| 2005/0162649 | A1 | 7/2005 | Kryszczynski et al. |

FOREIGN PATENT DOCUMENTS

| CN | 1796975 | 7/2006 |
| TW | M267449 | 6/2005 |

* cited by examiner

*Primary Examiner*—Tarifur Chowdhury
*Assistant Examiner*—Abdullahi Nur
(74) *Attorney, Agent, or Firm*—Jianq Chyun IP Office

(57) ABSTRACT

A multi-angle and multi-channel detecting device for detecting one or more than one samples is provided. The device has a light collector and a multi-channel kernel module. The light collector has a plurality of fiber probes arranged perpendicular to and/or inclined to the sample(s) so as to collect light signals. The kernel module is coupled to the light collector for detecting the sample(s).

15 Claims, 11 Drawing Sheets

MULTI-ANGLE AND MULTI-CHANNEL INSPECTING DEVICE

CROSS-REFERENCE TO RELATED APPLICATION

This application claims the priority benefit of Taiwan application serial no. 95129853, filed on Aug. 15, 2006. All disclosure of the Taiwan application is incorporated herein by reference.

BACKGROUND OF THE INVENTION

1. Field of the Invention

The present invention relates to a sample detecting device, and more particularly, to a multi-angle and multi-channel detecting device.

2. Description of Related Art

Liquid crystal display panel detecting technique includes measurements of optical parameters such as chromaticity and brightness and plays an important role in the quality control of liquid crystal displays. In particular, with the increasing area of the display panels and the increasing processing speed, a fast and accurate detection has become more and more important. At present, conventional panel detecting devices can be classified into single-point Fourier optics panel measuring devices and multi-point beam-split panel measuring devices.

FIG. 1 shows a technique disclosed in U.S. Pat. No. 6,804,001. The disclosed device is a combination of Fourier optics theory and a beam-split spectrum image spectrum measuring structure. Light rays emitted from a test object 2 pass through lens sets 6, 8 to reach a slit 16. After passing through the slit 16, the light rays are projected by a beam-split element 18 onto a two-dimensional photodiode array sensor 14. The element 18 is composed of several filters with different bandpass ranges. In addition, the device further includes a rotating mechanism 40 capable of rotating the slit 16 with different angles, so as to obtain chromaticity and brightness of a test point at different view angles. If information regarding the chromaticity and brightness of the entire test object is required, moving the probe or the sample in two dimension manner and combining the chromaticity and the brightness information at every point of the sample are necessary. However, this device or method spends a lot of time for performing the measurement, and can hardly be implemented for an on-line detection.

FIG. 2 shows a multi-point beam-split panel measuring device disclosed in U.S. Pat. No. 5,751,420. The disclosed device uses a beam-split image spectrum measuring structure. A panel 42 is placed on a plane at a work distance from an image capturing lens. Light rays emitted from the panel are guided by the lens into a spectrum imaging device. After passing through the beam-split element inside the device, light signals of different wavelengths are projected onto different positions of a two-dimensional photodiode array sensor, so that the spectrum image corresponding to different positions in the field of view on the object side are obtained. Although this method can simultaneously obtain multiple channels of spectrum information to achieve a multi-point spectrum measuring effect, the measurement can only be carried out at one specified view angle at a time. Thus, a mechanism for providing an angular swing of the probe or of the panel is required when measurements at different view angles are performed. The rotating and positioning mechanism not only is complicated, but the motion itself is also time-consuming. As a result, although this method has been applied to on-line detection, it is not a fully satisfied solution.

The single-point measuring method is currently the most widely used panel inspection technique. To measure the entire panel, the probe or the panel has to be moved two-dimensionally and a lot of measuring time is required. Furthermore, in order to obtain optical parameters such as chromaticity and luminance at different view angles, the probe or the panel must be swung with a relative angle. However, the rotating and positioning mechanism can be quite complicated and the mechanical motion takes a lot of time. Now, there are still no rapid measuring devices that satisfy the VESA measuring standard, and thus an innovative measuring method is urgently required.

SUMMARY OF THE INVENTION

Accordingly, the present invention is to provide a multi-angle and multi-channel detecting device capable of providing rapid multi-channel measurement and accurate multi-angle measurement, both of which can not be achieved at the same time in the conventional manner. Therefore, according to the present invention, a high spectrum resolution, multi-channel, multi-angle and real-time on-line detecting device is provided.

As embodied and broadly described herein, the multi-angle and multi-channel detecting device has a light collector and a multi-channel kernel module. The light collector has a plurality of fiber probes arranged in a direction perpendicular to and/or tilted with the sample(s) so as to collect light signals. The multi-channel kernel module is coupled to the light collector for detecting the sample(s).

The present invention also provides a multi-angle and multi-channel detecting device for detecting one or more than one sample. The multi-angle and multi-channel device has a plurality of light collectors and a plurality of single-channel kernel modules. Every light collector has at least one fiber probe arranged in a direction perpendicular to and/or tilted to the sample(s) so as to collect light signals. The single-channel kernel modules are respectively coupled to the light collectors for detecting the sample(s).

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
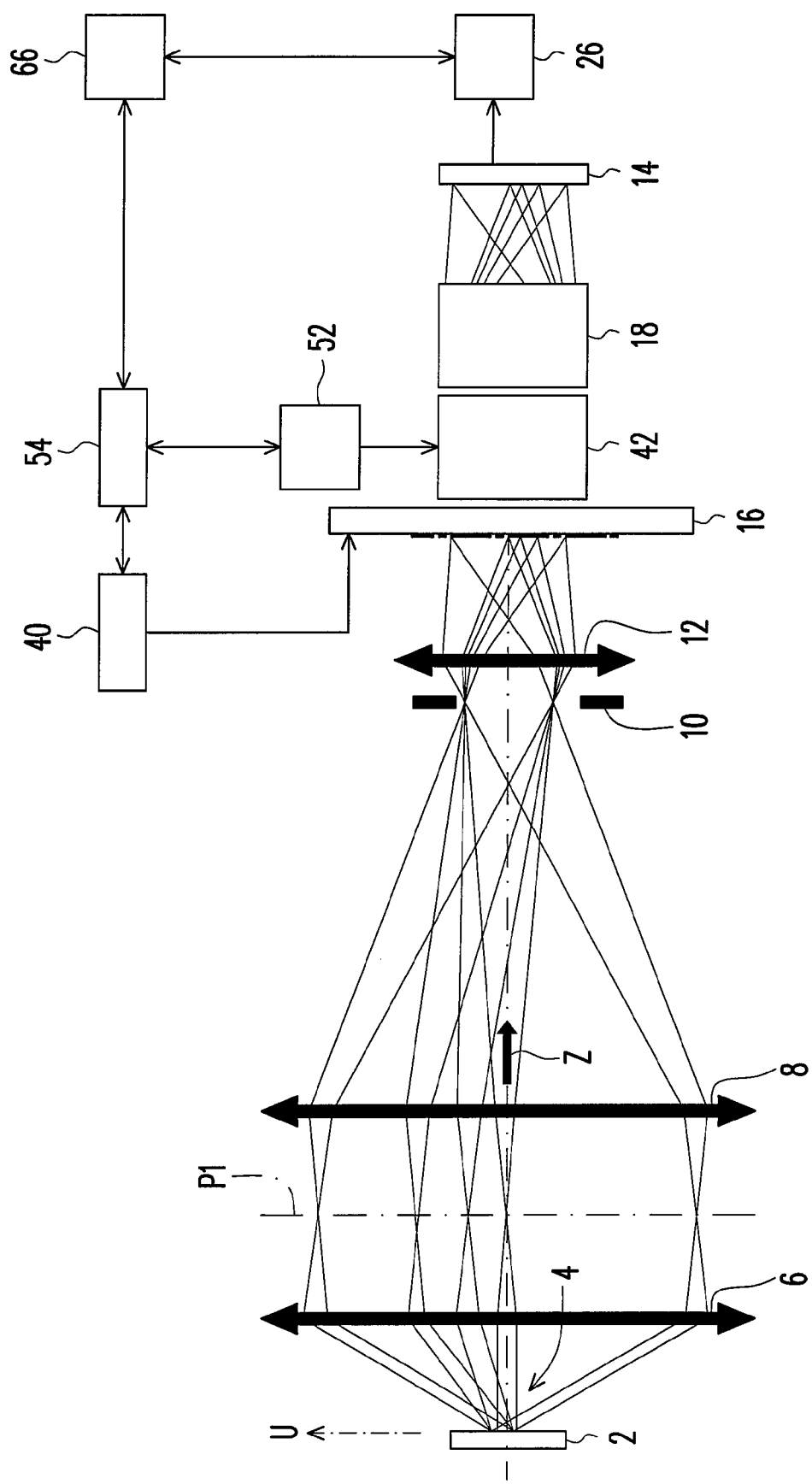
FIG. 1 illustrates a conventional single-point Fourier optics panel measuring device.
Figure 2:
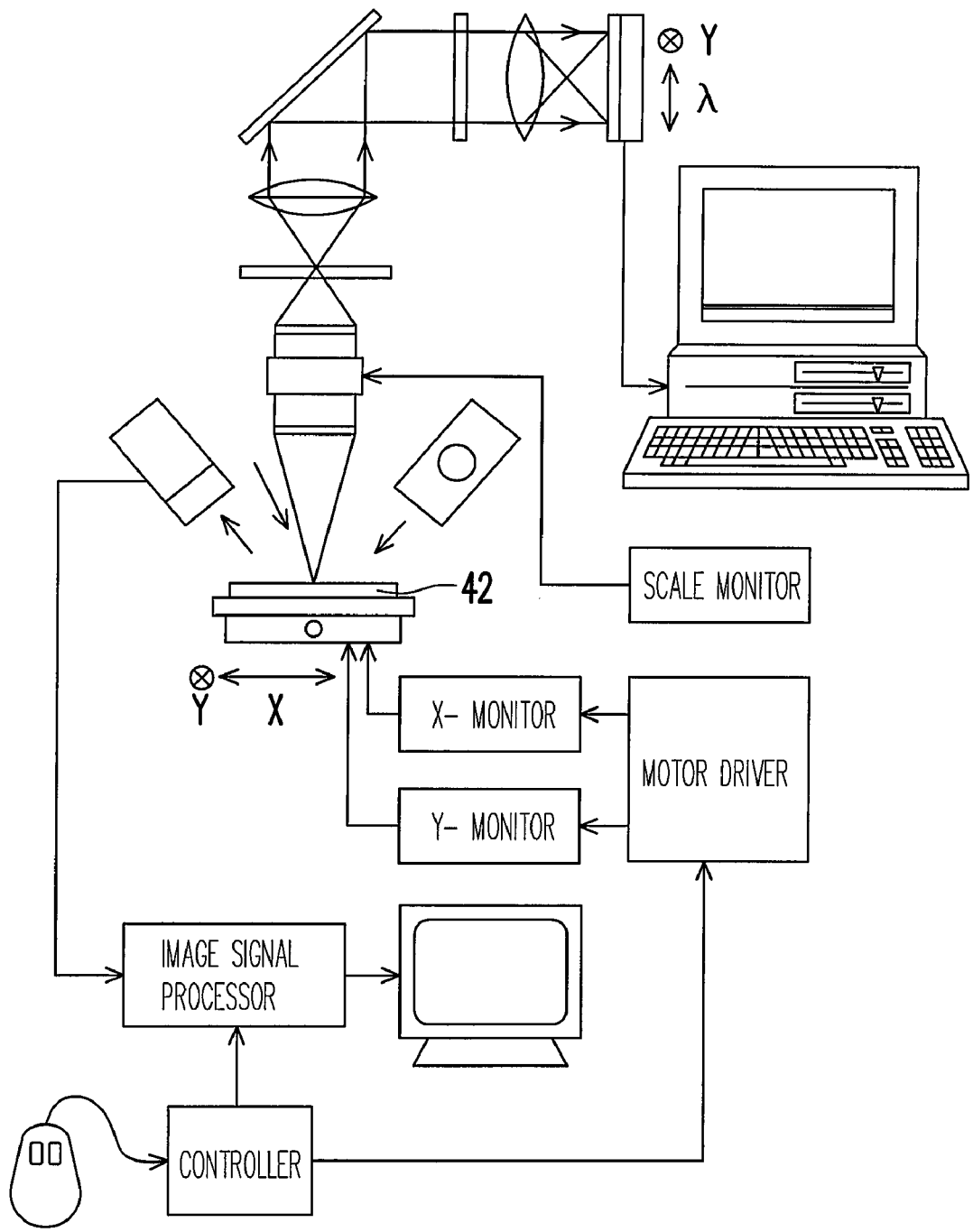
FIG. 2 illustrates a conventional multi-point beam-split panel measuring device.

Reference will now be made in detail to the present preferred embodiments of the invention, examples of which are illustrated in the accompanying drawings. Wherever possible, the same reference numbers are used in the drawings and the description to refer to the same or like parts.

The multi-angle and multi-channel detecting device of the present invention is a high-density multi-channel spectral imaging device that comprises a light collector capable of collecting light rays coming from different angles and a multi-channel kernel module. The light collector mainly comprises a multi-core fiber bundle.

Figure 3:
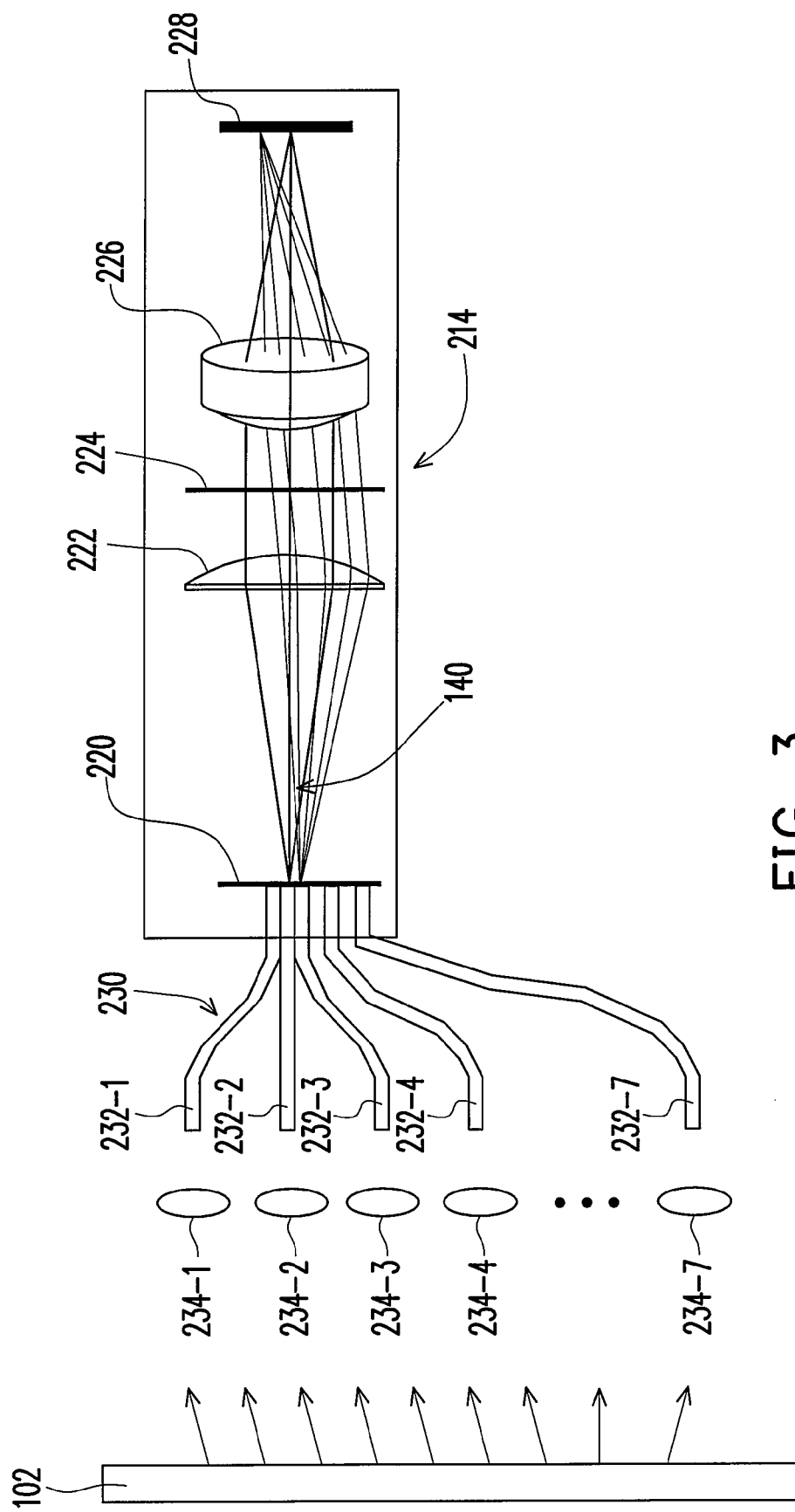
FIG. 3 is a schematic diagram showing the structure of a multi-angle and multi-channel detecting device according to one embodiment of the present invention.

FIG. 3 is a diagram showing the structure of a multi-angle and multi-channel detecting device according to one embodiment of the present invention. In the present embodiment, the multi-core fiber bundle 230 serving as the light collector may comprises a plurality of fiber probes 234-1, 234-2, . . . , 234-7 and a plurality of optical fibers 232-1, 232-2, . . . , 232-7. The multi-mode fiber bundle 230 is optically coupled to a multi-channel kernel module 214. To simplify the description, only 7 channels are depicted. In practice, the channel number can be increased or decreased according to the actual requirements in operation.

In the present embodiment, the multi-channel kernel module 214 may comprise an optical slit 220, a collimator lens group 222, a diffraction grating 224, a focusing lens group 226, and a two-dimensional array sensor 228, for example. The collimator lens group 222 can be an aspherical or a spherical collimator lens. The diffraction grating 224 can be a transmission diffraction grating or a reflection diffraction grating. The focusing lens group 226 can be a general focusing lens or an achromatic focusing lens. As shown in FIG. 3, the optical fibers 232-1, 232-2, . . . 232-7 in the multi-core fiber bundle 230 as the light collector are capable of transforming the principal light rays of the light rays emitted from various points on the sample 102 into light rays parallel to the optical axis 140 and then the light rays are incident to the optical slit 220 within the multi-channel kernel module 214. After passing through the optical slit 220, the light beam is further incident to the collimator lens group 222 and approximately becomes collimated light beam. Then, the collimated light beam is further incident to the diffraction grating 224 and focuses on the two-dimensional array sensor 228 through the focusing lens group 226.

Because light rays emitted from each point in the field of view on the object side (sample) 102 are received by the fiber bundle 230, the principle light rays incident to the module 214 from the fiber bundle 230 become parallel to the optical axis 140. The incident light beam is approximately collimated through the collimator lens group 222, so the light beam incident to the grating 224 is a collimated light beam, which satisfies the operational conditions of the grating. Additionally, the present embodiment further utilizes achromatic lens group 226 and rotation of the sensor 228 to adjust an inclined position of the chromatic aberration surface, so that the chromatic aberration at each wavelength band can also be eliminated. Through the foregoing structure, the light rays emitted from the object side only has tiny aberration, so that the spectral resolution is considerably enhanced to achieve the purposes of high density and multiple channels.

The optical fibers 232-1, 232-2, . . . , 232-7 of the multi-core fiber bundle 230 are flexible so that light receiving angles of the fiber probes 234-1, 234-2, . . . , 234-7 can be bent into various angles to match the actual requirements of the detection and to achieve the multi-angle detection. In general, each of the fiber probes 234-1, 234-2, . . . , 234-7 can be constructed by lens designed with different solid angles according to the requirements for performing multi-angle measurements.

Next, taking a panel detection for a liquid crystal display for example, the installation and operation of the multi-angle and multi-channel detecting device of the present embodiment are described.

Figure 4A:
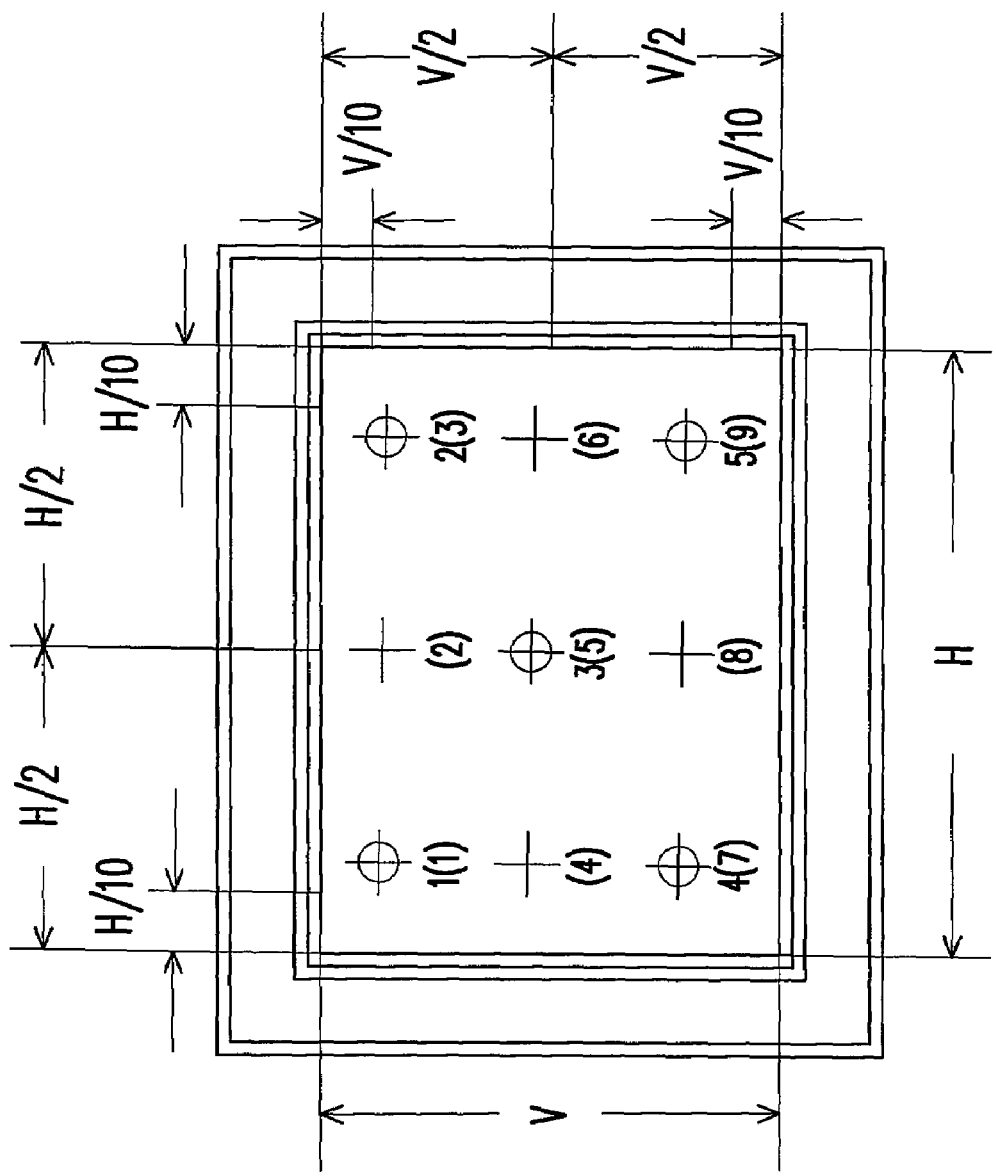
FIG. 4A is a schematic diagram showing measuring points of a panel under the VESA specification.

In the beginning, the VESA specification regarding the panel measurement is explained with reference to FIGS. 4A and 4B. FIG. 4A shows a front view of the panel. In the VESA specification, the length H and width V of the panel are used to define five or nine specific points for performing a panel uniformity measurement. In FIG. 4A, the numbers 1 to 5 indicate the five specific points for performing the measurement, and the numbers (1) to (9) indicate the nine specific points for performing the measurement. For the central point of the panel (point 3 or point (5) in FIG. 4A), measurements at four different angles are further required in addition to the measurement that the probe is perpendicular to the panel. The other measuring points respectively need one measurement at one angle. Namely, the measurement is made with the probe set perpendicular to the panel.

Figure 4B:
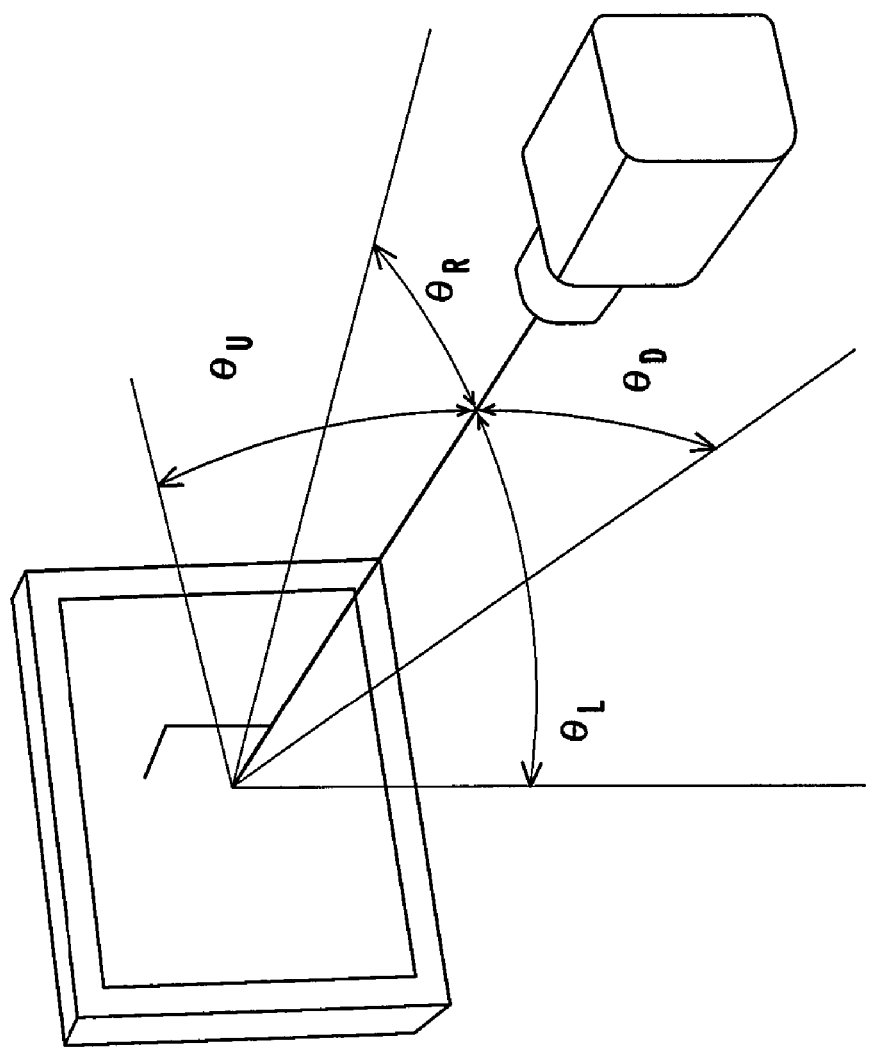
FIG. 4B is a schematic diagram showing the other four measurements at different angles for a central point of the panel in FIG. 4A.

FIG. 4B is a schematic diagram showing the measurements of the central point of the panel at four other angles. The angles are up angle $\theta_U$, down angle $\theta_D$, left angle $\theta_L$ and right angle $\theta_R$ and their corresponding angles with respect to the normal line of the panel are $\theta_U=15°$, $\theta_D=10°$, $\theta_L=30°$ and $\theta_R=30°$. Through the measurements at the specific angles, whether the panel under test satisfies the VESA specification can be determined.

Figure 6:
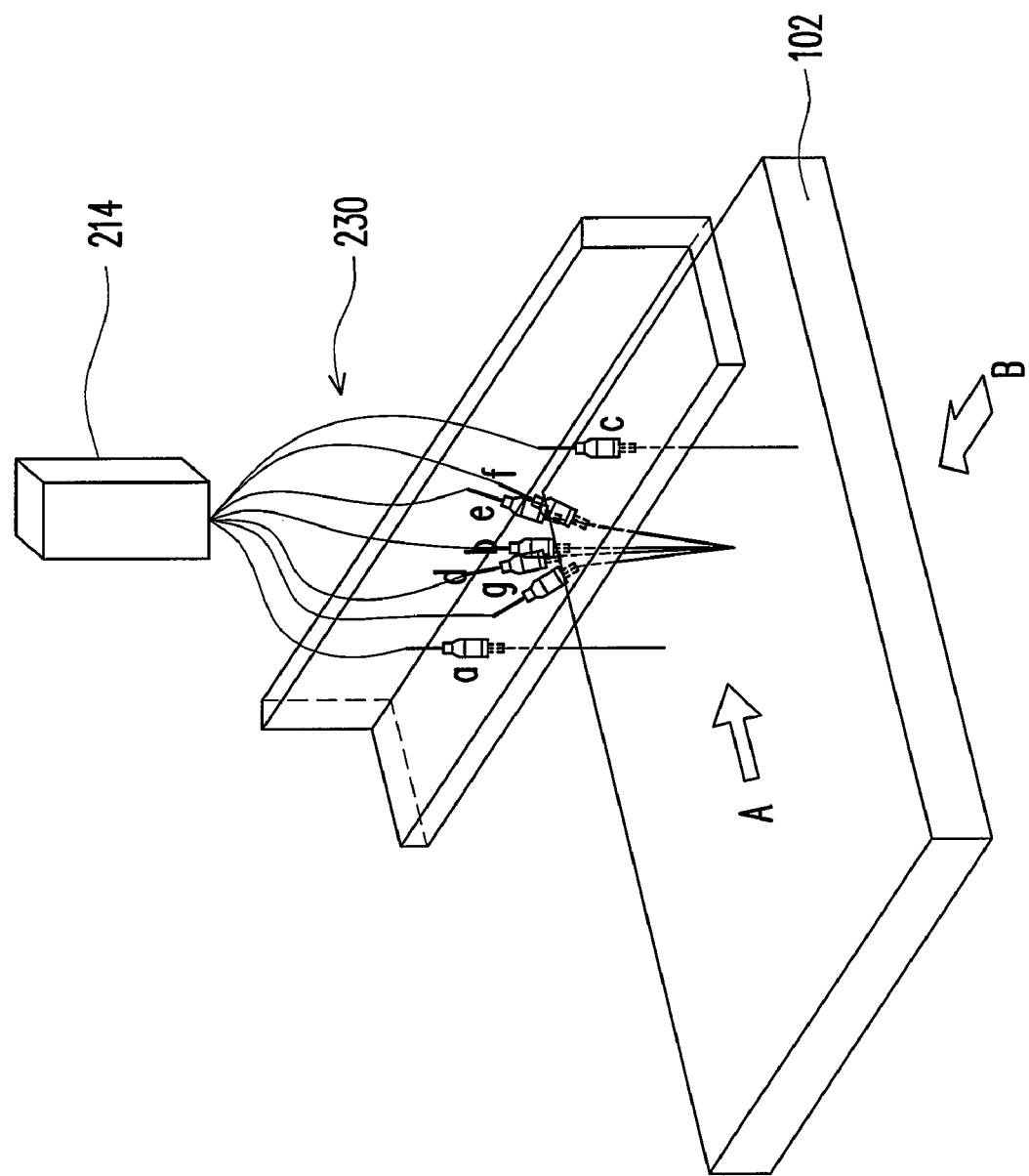
FIG. 6 is a schematic diagram of a one-dimensional multi-angle and multi-channel detecting device according to the first embodiment of the present invention.

Next, the installation and the operation of the multi-angle and multi-channel detecting device of the present embodiment are explained. FIG. 6 is a schematic diagram showing an application using the multi-angle and multi-channel detecting device according to one embodiment of the present invention. In this embodiment, seven channels are depicted. As shown in FIG. 6, the multi-core fiber bundle 230 in FIG. 3 is fixed by fixing units to position the probes, so as to form a panel detecting device as shown in FIG. 6.

The multi-channel kernel module 214 uses the multi-core fiber bundle 230 as a light collector. The panel 102 serving as a sample is placed at the focus positions of the fiber probes (a, b, c, d, e, f, g). The fiber probes (a, b, c) of the multi-core fiber bundle 230 are placed perpendicular to the panel 102 while the fiber probes (d, e, f, g) are placed not perpendicular to the panel 102. Hence, a multi-channel and multi-view-angle measurement of the panel spectrum can be simultaneously performed.

Figure 5:
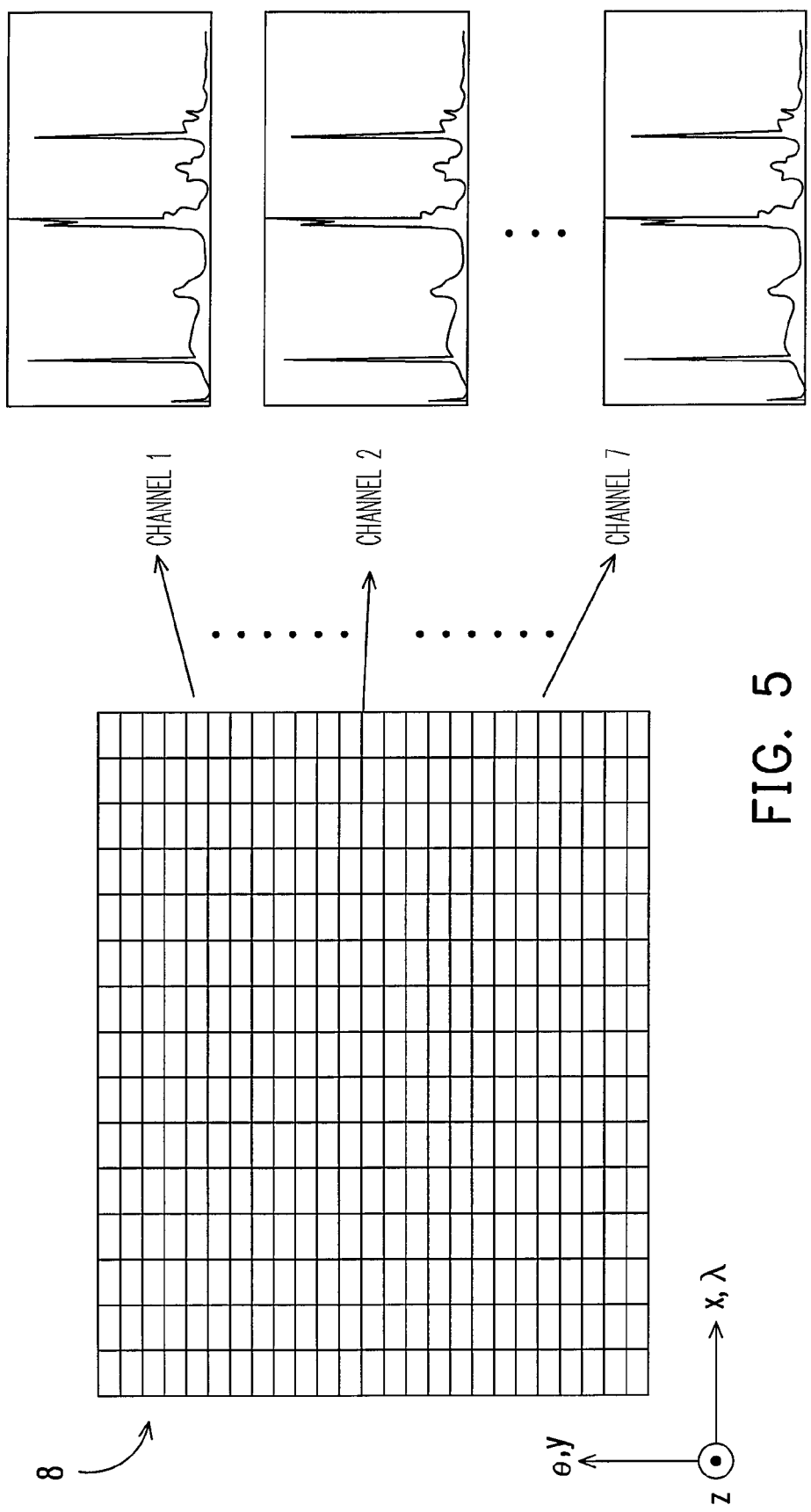
FIG. 5 shows a multi-channel spectrum on a two-dimensional array sensor.

After the light emitted from the panel (the sample) is received by the fiber probes, the light signals are transmitted through the optical fibers of the multi-core fiber bundle 230 to the two-dimensional array sensor 228 inside the multi-channel kernel module 214, so as to obtain images. As shown in FIG. 5, the two-dimensional array sensor 228 can be a charge-coupled device (CCD), for example. One of the axes (such as the y axis) corresponds to spatial channel and information of the view angle while the other axis (such as the x axis) corresponds to the spectral information. As shown in the right half portion of FIG. 5, the two-dimensional array sensor 228 shows the spectral information corresponding to various wavelengths λ of each channel. Here, channel 1 corresponds to the light signals received by the fiber probe a, channel 7 corresponds to the light signals received by the fiber probe g, and so on.

In the foregoing detecting device, through the combination of the multi-channel kernel module 214 and the multi-core fiber bundle 230, and the use of the aspherical collimator lens group 222, the achromatic focusing lens group 226, and the rotation of the two-dimensional array sensor 228, the signals of all seven channels collected by the multi-core fiber bundle 230 can be separated on the two-dimensional array sensor 228 as shown in FIG. 5, so as to obtain the individual spectrum of channel 1 to channel 7. Therefore, the characteristics of multi-channel and multi-angle can simultaneously exist.

Figure 7A:
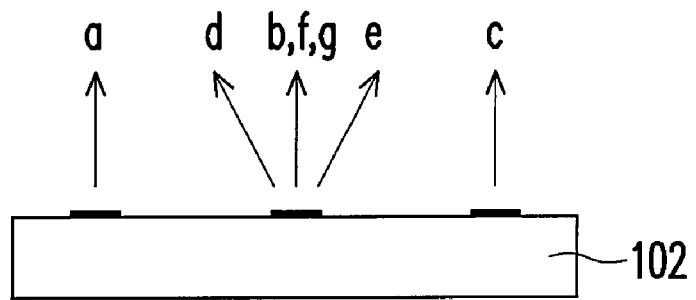
FIG. 7A is a schematic diagram showing the arrangement configuration and angle distribution of the fiber probes looked from the direction A in FIG. 6.
Figure 7B:
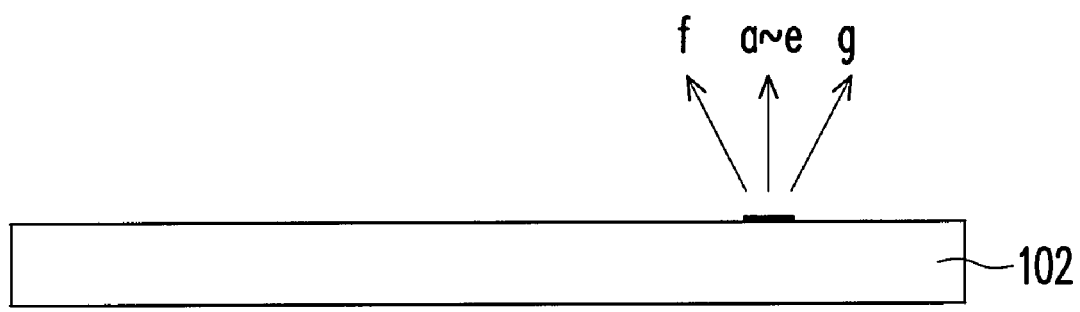
FIG. 7B is a schematic diagram showing the arrangement configuration and angle distribution of the fiber probes looked from the direction B in FIG. 6.
Figure 9A:
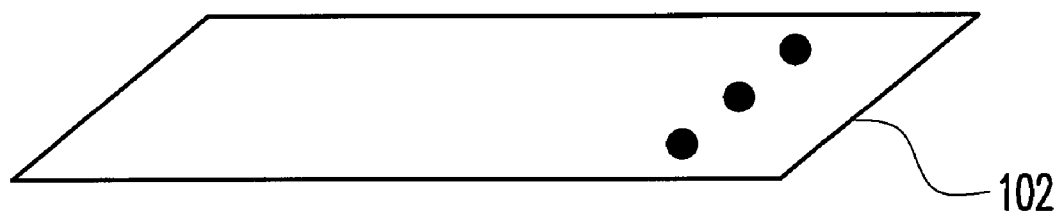
FIG. 9A is a schematic diagram showing measuring points of a one-dimensional distribution on a sample and measured by the discrete multi-channel fiber probes of the multi-angle and multi-channel detecting device in FIG. 6.

The fiber probes (a~g) in FIG. 6 has a one-dimensional discrete multi-channel and multi-angle arrangement as shown in FIG. 9A. FIG. 7A is a diagram showing the arrangement configuration and angle distribution of the fiber probes looked from the direction A in FIG. 6. FIG. 7B is a diagram showing the arrangement configuration and angle distribution of the fiber probes looked from the direction B in FIG. 6. As shown in FIG. 7A, the fiber probes are arranged in an order of a, d, (b, f, g), e, c when looked from the direction A, while the fiber probes are arranged from the direction B in an order of f, a~e, g as shown in FIG. 7B. Accordingly, the light-receiving angles of the fiber probes a~g are designed and arranged to satisfy the VESA specification. In other words, the fiber probes a~g in FIG. 6 is capable of measuring one-dimensional points such as the points (2), (5), (8) or the points 1, 3, 5 in FIG. 4A. For the central point, the light signals from the non-perpendicular direction can also be measured in addition to the measurement at the perpendicular direction. In addition, by moving the fiber probes a~g or the panel 102 to be tested three times and performing three measurements, spectrum covering the entire panel is measured under the VESA specification.

Figure 8:
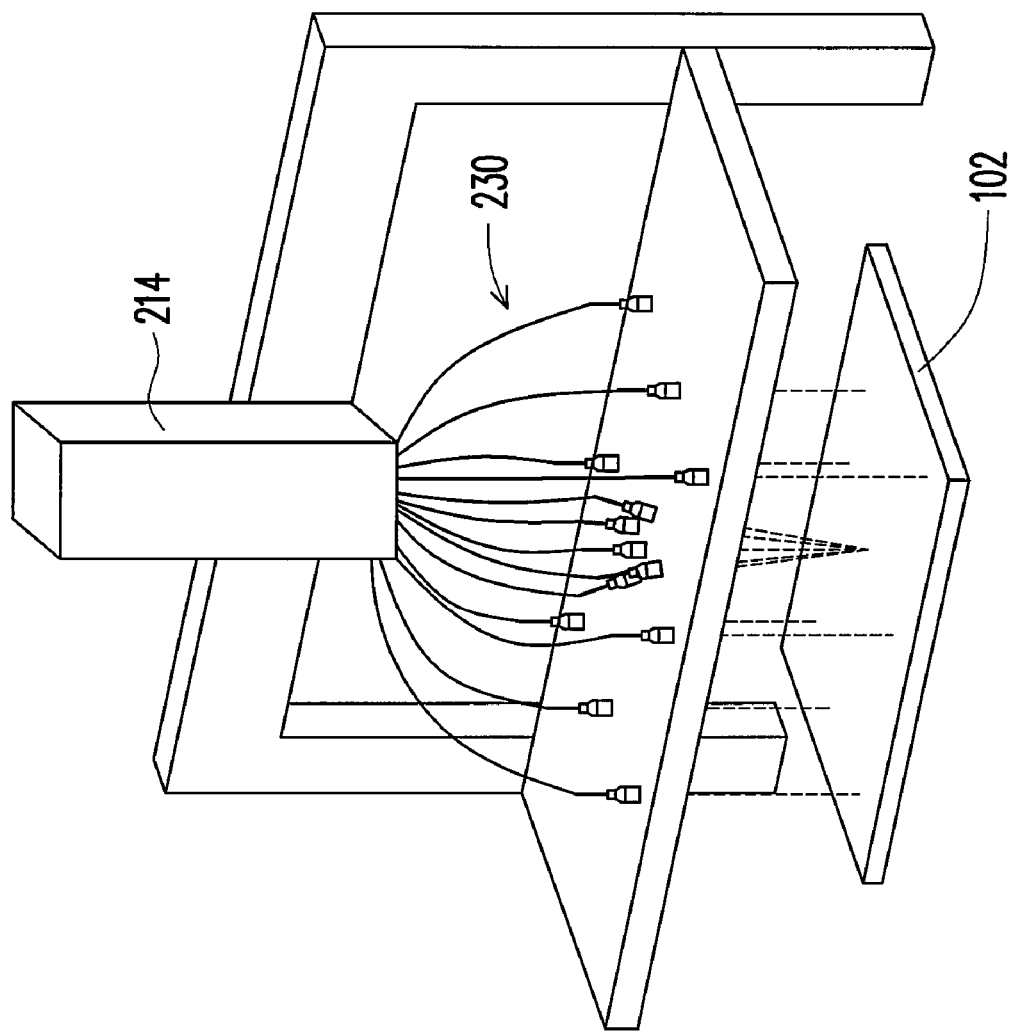
FIG. 8 is a schematic diagram of a two-dimensional multi-angle and multi-channel detecting device according to the second embodiment of the present invention.
Figure 9B:
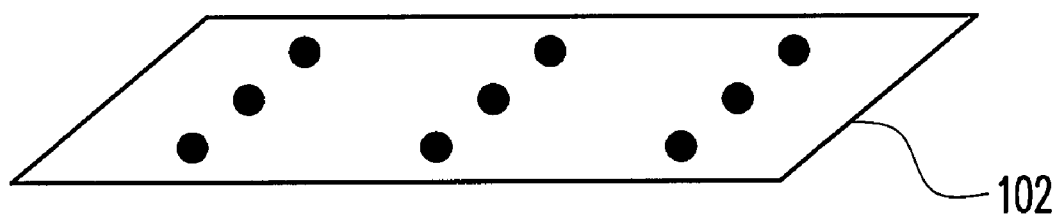
FIG. 9B is a schematic diagram showing measuring points of a two-dimensional distribution on a sample and measured by the discrete multi-channel fiber probes of the multi-angle and multi-channel detecting device in FIG. 8.

FIG. 8 is a schematic diagram of a two-dimensional multi-angle and multi-channel detecting device system according to the second embodiment of the present invention. As shown in FIG. 8, the fiber probes are distributed as a 13-channel array over the panel to be tested. Without having to scan (to move) the fiber probes or the panel to be tested, a two-dimensional and discrete multi-channel panel spectrum of the sample is obtained at a time under the VESA specification. As show in FIG. 9B, the measurement points corresponding to the fiber probes are arranged as a two-dimensional discrete distribution. As shown in FIGS. 8, 4A and 9B, nine of the 13 fiber probes can be set perpendicular to the points (1)-(9) in FIG. 4A. The other four fiber probes are set in a non-perpendicular manner to measure the central point (5) and the angles of the fiber probes are arranged according to the VESA specification. Thus, the two-dimensional fiber probe distribution shown in FIG. 8 can carry out a panel measurement in a single operation. Namely, the multi-angle and multi-channel measurement can be performed rapidly.

After the multi-channel spectral information as described in FIG. 6 or 8 is obtained, the obtained information is further calculated by a chromaticity algorithm, and the multi-channel and multi-angle optical parameter information of the panel can be rapidly and accurately obtained. This manner is much faster than the existing method of performing a single point measurement for 13 times (13 different points).

Figure 10:
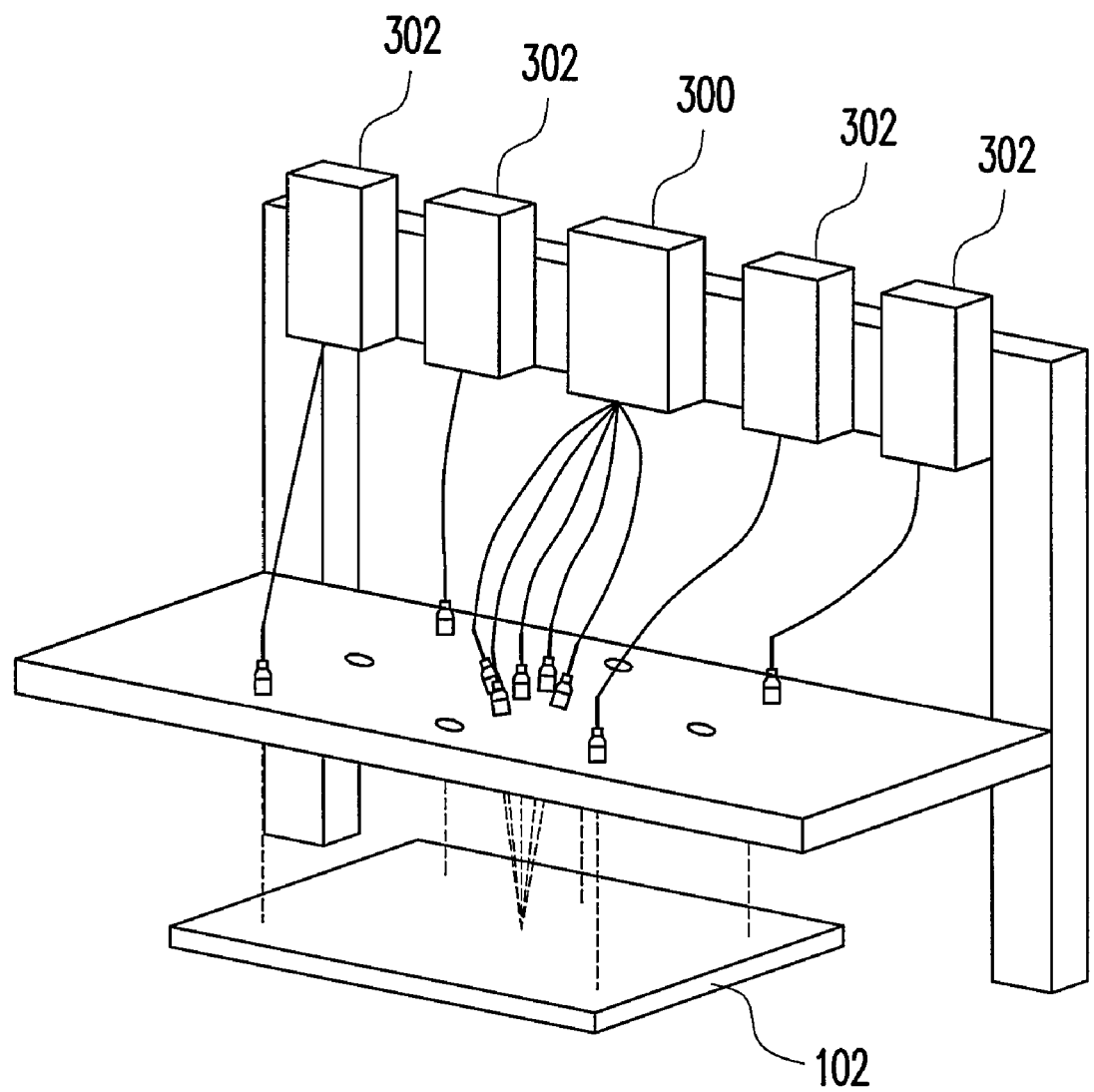
FIG. 10 is a schematic diagram of a two-dimensional multi-angle and multi-channel detecting device according to another embodiment of the present invention.

In the foregoing multi-channel kernel module 214, one kernel module includes all required channels. However, in actual applications, the multi-channel and multi-angle detecting device can be used as a single-channel and single-angle detecting device. FIG. 10 shows a variation example according to one embodiment of the present invention. As shown in FIG. 10, the foregoing panel uniformity measurement according to the VESA specification for the chromaticity at different view angles at five different points on the panel is still used as an example. Five detecting devices 302, 300 with each device having a light collector are used. The detecting device 300 performs measurements at five different view angles for the central point of the panel. The other four detecting devices 302 are used to perform single-channel and single-view-angle measurements of the other four points.

In the foregoing description, the VESA specification of a display panel serves as an example for operating the multi-angle and multi-channel detecting device in the present invention. However, the applications of the present invention are not limited to panel detection. Any detection technique that uses a spectrum analyzer or needs multi-angle measurement can use the device of the present invention. Thus, a single-channel and single-view-angle measurement and a multi-channel and multi-view-angle measurement can be developed according to the present invention.

The description in the foregoing embodiments is based on the VESA specification for display panel. Therefore, for measurements that satisfy the VESA specification, some of the fiber probes are disposed at an inclined angle. However, for other measurement specifications or objects, it may not be necessary to arrange the fiber probes at an inclined angle. In other words, the fiber probes can be adjusted according to the actual condition so that all or some of the fiber probes are disposed in a direction perpendicular to the sample surface or none of the fiber probes are disposed in this way.

In addition, the present invention can be applied to transparent samples. In other words, the structure as shown in FIGS. 6, 8 and 10 can be slightly modified to form a transmissive structure in order to perform detection for the transparent sample. Because the sample is transmissive, light beam(s) incident on the sample will not follow the original path as shown in the figures to return to the multi-channel kernel module or each of the single-channel kernel modules. Therefore, for the transmissive structure, the optical fiber(s) of the multi-channel kernel module or single-channel kernel modules needs to be modified into unidirectional. Furthermore, on the other side of the sample and at locations corresponding to the light emitting ends, a multi-channel kernel module or single-channel kernel modules are similarly set for receiving light beam that passes through the transparent sample. Hence, through a suitable modification, the present invention not only can be applied to detect the opaque samples, but can be used to detect transparent samples as well.

Other applications of the present invention are to measure the chromaticity and luminance of a flat panel display (FPD), measure the chromaticity and luminous intensity of the die of the light emitting diode (LED) of a semiconductor wafer, and detect the photoluminescence (PL) of a semiconductor wafer, such as a Si-based epi-layer, and a group III-V based epi-layer.

Additionally, supposing that the detection wavelength of the two-dimensional array sensor is designed to use a near infrared (NIR) wavelength, the two-dimensional array sensor can be used to the spectrographic detection of the pharmaceutics or textile. If the present invention further integrates with an optical coherence tomography (OCT) technology, the two-dimensional array sensor can be used to measure the three-dimensional configuration of inner skin. If further integrating with the polarization technology, the two-dimensional array sensor can be used to detect the characteristics of the birefringence of an FPD polarizer and measure the parameters of the spectroscopy ellipsometry of a thin film sample. Any multi-channel spectrographic detecting technologies are protected by the claims of the patent as long as the technologies employ multi-core optical fiber bundles or image focusing lenses as light collectors, especially image-side telecentric lenses.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A multi-angle and multi-channel detecting device for detecting one or more than one liquid crystal display (LCD) panel, the multi-angle and multi-channel detecting device comprising:
    a light collector having a plurality of fiber probes, wherein the fiber probes are arranged in a direction perpendicular to and/or tilted with the LCD panel so as to collect light signals from the LCD panel; and
    a multi-channel kernel module, comprising an optical slit, a collimator lens group, a diffraction grating, a focusing lens group and a two-dimensional array sensor sequentially disposed along an optical path of the multi-channel kernel module, wherein the multi-channel kernel module is coupled to the light collector for receiving the collected light signals from the light collector to obtain individual spectrum by guiding the light signals through the fiber probes, the optical slit, the collimator lens group, the diffraction grating, and the focusing lens group orderly to the two-dimensional array sensor, such that the LCD panel is detected.

2. The device as claimed in claim 1, wherein by using the light collector, light beams incident to the multi-channel kernel module are parallel to an optical axis of the multi-channel kernel module.

3. The device as claimed in claim 1, wherein the fiber probes are arranged to form a one-dimensional discrete array.

4. The device as claimed in claim 1, wherein the fiber probes are arranged to form a two-dimensional discrete array.

5. The device as claimed in claim 1, wherein the collimator lens is an aspherical collimator lens group or a spherical collimator lens group, the diffraction grating is a transmissive diffraction grating or a reflective diffraction grating, and the focusing lens group is a commercial focusing lens group or an achromatic focusing lens group.

6. The device as claimed in claim 5, wherein the achromatic focusing lens group and the two-dimensional array sensor are capable of rotating to tilt relative to an optical axis of the multi-channel kernel module.

7. The device as claimed in claim 1, wherein the light collector is a multi-core fiber bundle comprising a plurality of optical fibers respectively connected to the fiber probes.

8. A multi-angle and multi-channel detecting method for inspecting one or more LCD panels, the multi-angle and multi-channel detecting method comprising:
    providing a plurality of fiber probes disposed at different angles;
    collecting light signals from the LCD panel by using the fiber probes; and
    providing the collected light signals to a multi-channel kernel module, wherein the multi-channel kernel module comprises an optical slit, a collimator lens group, a diffraction grating, a focusing lens group and a two-dimensional array sensor sequentially disposed along an optical path of the multi-channel kernel module, such that the collected light signals are transmitted from the fiber probes, the optical slit, the collimator lens group, the diffraction grating, and the focusing lens group orderly to the two-dimensional array sensor so as to obtain individual spectrum of the collected light signals.

9. The method as claimed in claim 8, wherein the fiber probes are arranged to form a one-dimensional discrete array.

10. The method as claimed in claim 8, wherein the fiber probes are arranged to form a two-dimensional discrete array.

11. A multi-angle and multi-channel detecting device for detecting one or more LCD panels, the multi-angle and multi-channel detecting device comprising:
    a plurality of light collectors with each of the light collectors having at least a fiber probe, wherein the fiber probes are arranged in a direction perpendicular to and/or tilted with the LCD panel(s) so as to collect light signals from the LCD panel(s); and
    a plurality of single-channel kernel modules, respectively coupled to the light collectors, wherein each of the single-channel kernel module comprises an optical slit, a collimator lens, a diffraction grating, a focusing lens and a two-dimensional array sensor sequentially disposed along the optical path of the single-channel kernel module, such that the LCD panel is detected by receiving the light signals through the fiber probes, the optical slit, the collimator lens group, the diffraction grating, the focusing lens group and the two-dimensional array sensor orderly in order to obtain individual spectrum of the light signals.

12. The device as claimed in claim 11, further comprising at least one multi-channel kernel module for performing a LCD panel(s) detection through the light collectors, and by using the light collectors, light beams incident to the multi-channel kernel module are parallel to an optical axis of the multi-channel kernel module.

13. The device as claimed in claim 11, wherein the fiber probes are arranged to form a one-dimensional discrete array or a two-dimensional discrete array.

14. The device as claimed in claim 11, wherein the collimator lens is an aspherical collimator lens or a spherical collimator lens, the diffraction grating is a transmissive diffraction grating or a reflective diffraction grating, the focusing lens is a commercial focusing lens or achromatic focusing lens.

15. The device as claimed in claim 14, wherein the achromatic focusing lens and the two-dimensional array sensor are capable of rotating to tilt relative to an optical axis of the single-channel kernel module.

* * * * *